United States Patent [19]
Pedroso et al.

[11] 4,230,031
[45] Oct. 28, 1980

[54] BIOHAZARD CONTAINMENT APPARATUS AND METHOD

[75] Inventors: Raul I. Pedroso; Robert E. Auer, both of Miami, Fla.

[73] Assignee: Coulter Electronics, Inc., Hialeah, Fla.

[21] Appl. No.: 900,103

[22] Filed: Apr. 26, 1978

[51] Int. Cl.³ .............................................. F23J 11/00
[52] U.S. Cl. ........................ 98/115 LH; 55/DIG. 18; 209/3; 422/104
[58] Field of Search ...................... 98/115 R, 115 LH; 422/104; 209/3; 55/DIG. 18

[56] References Cited

U.S. PATENT DOCUMENTS

| | | | |
|---|---|---|---|
| 2,627,220 | 2/1953 | Morrow | 98/115 LH |
| 2,907,263 | 10/1959 | Müller | 98/115 LH |
| 3,022,718 | 2/1962 | Thompson | 98/115 LH |
| 3,380,584 | 4/1968 | Fulwyler | 209/127 R |
| 3,710,933 | 1/1973 | Fulwyler | 209/3 |
| 3,963,606 | 6/1976 | Hogg | 209/3 |

Primary Examiner—Ronald C. Capossela
Attorney, Agent, or Firm—Gerald R. Hibnick

[57] ABSTRACT

The containment of biohazardous substances, which may exist in the streams of sample material that are being separated in air into droplets in a testing chamber of equipment, such as cell sorters and cytofluorometers, is attained by subjecting the testing chamber to negative air pressure, so that inward air flow at the open face of the chamber is sufficient to inhibit biohazardous substances from exiting out from the face of the chamber. A region of air stagnation is created around the sample streams so that the streams are not deflected from their paths, such paths being pertinent to their testing of the biological sample material. The air stagnation region is formed by interposing an air diverter between the sample streams and the air flow exhaust port at the rear of the testing chamber.

6 Claims, 4 Drawing Figures

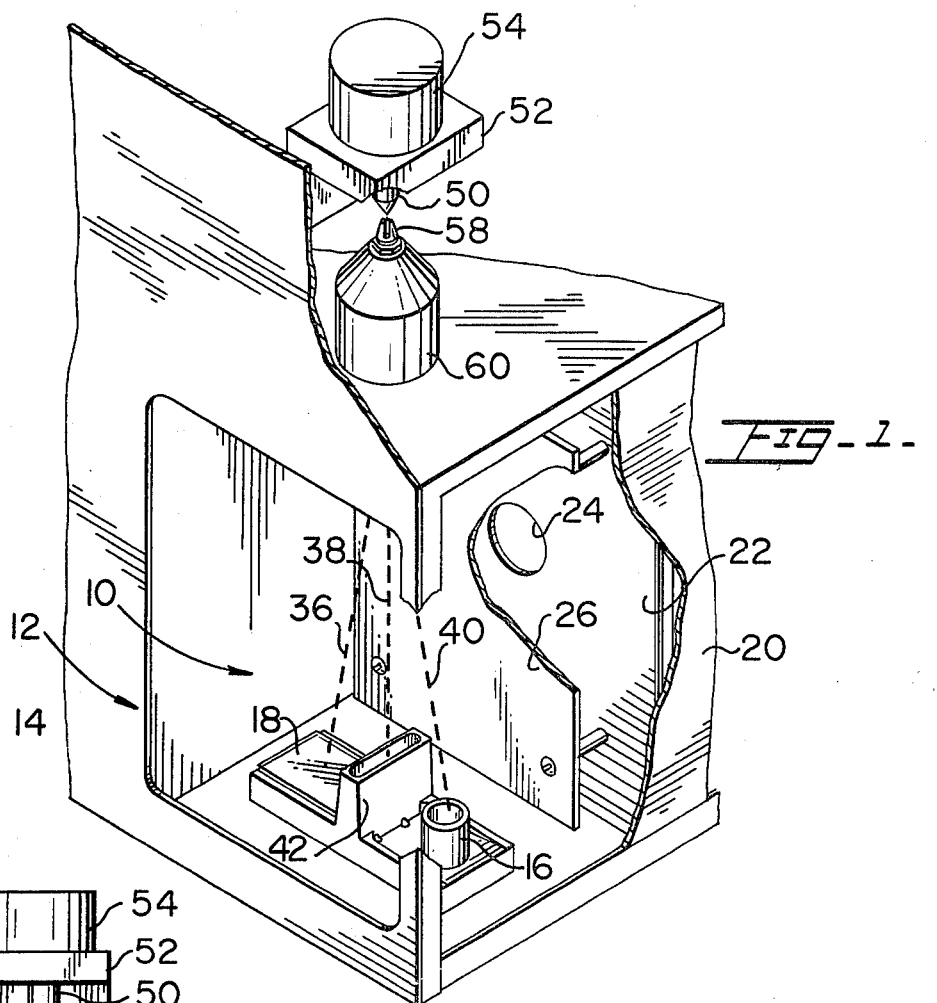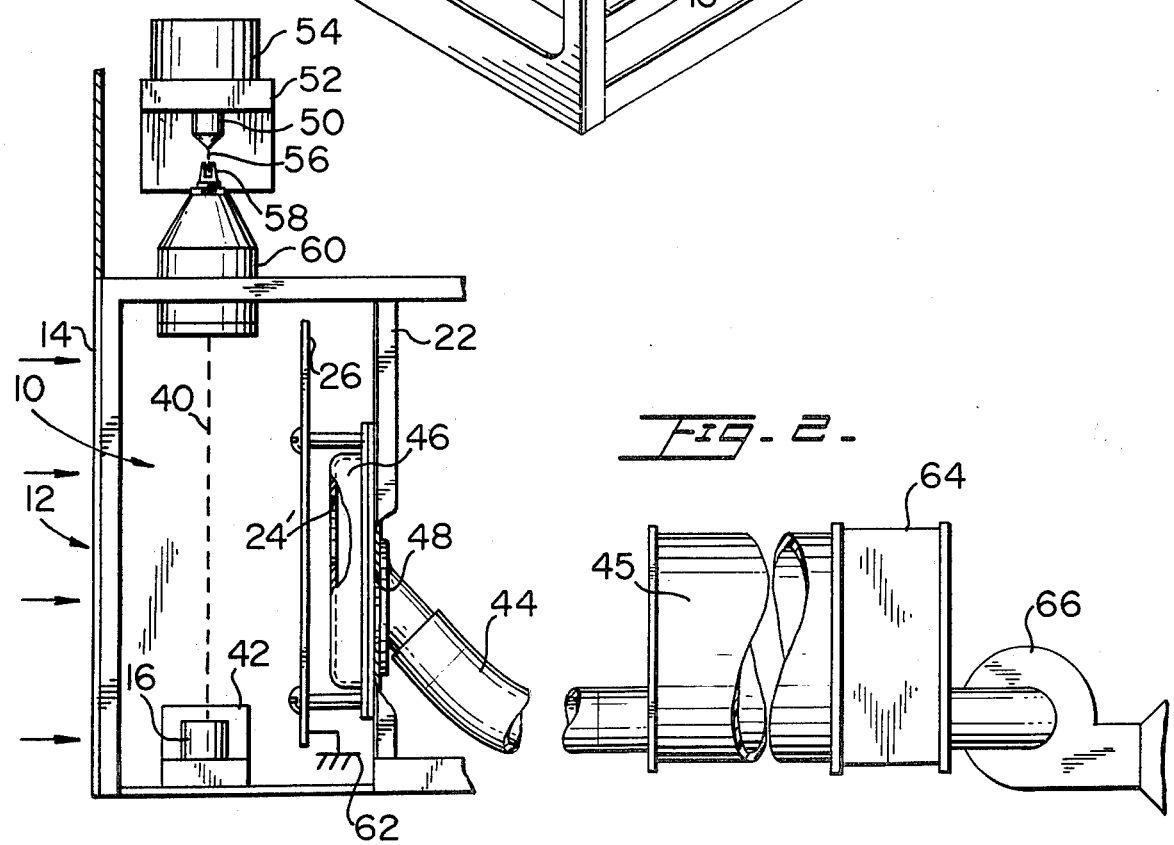
Fig. 1.
Fig. 2.

BIOHAZARD CONTAINMENT APPARATUS AND METHOD

BACKGROUND OF THE INVENTION

This invention concerns apparatus and method for containment of biohazardous substances in the environment of biological sample research and testing equipment. More specifically, this invention is directed to the containment of hazardous substances which may enter the air environment of equipment in which very thin streams of sample material are injected into air and, as a result, there are generated aerosols and fumes which can carry the hazardous substances into the proximate environment and be inhaled by humans or otherwise expose them to danger.

The risk to man from possible exposure to biohazardous substances, including carcinogenic chemicals and onceogenic agents, has been of increasing concern to those in the medical and biological research and testing fields and governmental agencies involved in establishing safety standards. Some sample materials in biological research, immunilogical studies and testing are known to contain biohazardous substances, including carcinogens. For example, in the field of cytology and hematoloy, there can be danger related to hepatitis, various living disease state cells, disassociated tumors, lymphocytic leukemia, solvent vapors, bacteria, and cell stains such as propidium iodide.

Generally speaking, for the containment of air borne biohazardous substances, there are known methodology and structures, including exhaust air treatment, decontamination and disposal, glove boxes, laminar flow safety cabinets, etc. However, these have limitations and establish conditions which could be detrimental to the integrity of the testing conditions; for example, the positioning of the thin streams of biological sample material during sorting. Such streams of sample are typical in equipment which analyze and sort minute particles and cells. One example of such sorting and analyzing equipment is disclosed in U.S. Pat. Nos. 3,380,584; 3,710,933 and 3,963,606; a commercial embodiment thereof being sold as the Coulter ® Model TPS Cell Sorter. The mark "Coulter" is the Registered trademark, registration No. 995,825 of Coulter Electronics, Inc. of Hialeah, Florida.

One function of the Coulter ® Model TPS Cell Sorter is to segregate the microscopic biological particles in the sample on the basis of measurements of the particles on a one by one basis as they flow in a liquid stream past parameter sensors. Once sensed, the sample stream is jetted into the air to form a droplet stream and is passed into the region of charging electrodes and deflection plates. Signals from the sensors for each particle determine the charging characteristic applied to each droplet, such that the magnitude of deflection can be regulated to cause particles with specific characteristics to be deflected into a predetermined path for collection in a container or onto a microscope slide. Several different particle droplet paths can be achieved. Now therefore, if the trajectories of the falling droplets are altered by the typical air flow exhausting of biohazard equipment, then the sorting function will be thwarted.

The Department Of Health Education And Welfare, in DHEW Publication No. (NIH) 76-900 of June 2, 1975 entitled "National Cancer Institute Safety Standards for Research Involving Chemical Carcinogens", recommends that open face hoods and laminar flow biological safety cabinets operate so that the average linear face velocity be at least one hundred feet per minute. At this velocity, it has been found that the droplet streams of the Coulter ® Model TPS Cell Sorter become detrimentally deflected and it may be found that similar cell sorters of other manufacture suffer the same or other problems with conventional biohazard containment apparatus.

SUMMARY OF THE INVENTION

The invention provides a biohazard containment apparatus and method which permits a high linear face velocity of air to pass into the chamber in which the fine sample streams of a cell sorter or like equipment are being processed, without any significant detrimental deflection of the sample streams. Inward of the forward or front face of the chamber there is established a region of air stagnation which surrounds the sample streams and protects them from undesired deflection by the containment air flow. The region of air stagnation is created by interposing an air flow diverter between the sample streams and the exhaust port at the rear of the chamber.

BRIEF DESCRIPTION OF THE DRAWINGS

FIG. 1 is a perspective view, somewhat pictorial, of the sample sorting chamber of a cell sorting device including the air diverter member of the invention;

FIG. 2 is a side view of the sorting chamber with diverter, an adjacent portion of the cell sorter, and filter and air flow elements of the biohazard containment apparatus.

DESCRIPTION OF THE PREFERRED EMBODIMENTS

Figure 3:
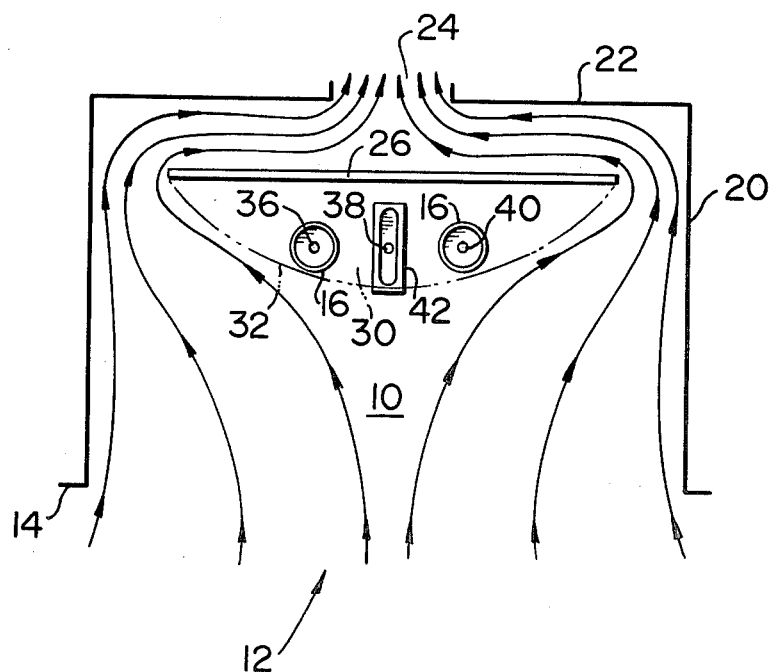
FIGS. 3 and 4 are top views, somewhat diagrammatic, showing air flow around two embodiments of the diverter member.

FIG. 1 illustrates, somewhat pictorially, the sorting chamber 10 of a cell sorter. The chamber 10 has large opening 12 in its forward wall 14, by way of which the laboratory operator can monitor the sorting process, insert and retrieve sample containing collection cups 16 and slides 18 and perform other testing requirements. Side wall 20 is shown broken away in FIG. 1 and is removed in FIG. 2 to reveal the contents of the chamber 10, but in fact completely closes its side of the chamber. The opposite side wall, top, bottom, and rear wall 22 of the chamber also are closed to air flow, except for an air and aerosol exhaust port 24 in the rear wall, so that containment air flow will enter through the opening 12, as shown by air flow arrows in FIGS. 2–4, such arrows not having reference numbers, move rearwardly and exit through the port 24.

An air flow diverter member 26 is spaced from the rear wall 22 by suitable hardware. In FIGS. 1–3 the diverter is a planar member, lying parallel to the rear wall, but in FIG. 4 has forwardly extending sides 28 which enhance the formation of an air stagnation region 30 which is bounded by the air flow member 26 and generally by the phantom lines 32 and 34 as depicted respectively in FIGS. 3 and 4. Droplet streams 36, 38 and 40 all lie within the stagnation region. The stream 38 typically is not deflected by the sorting process and falls into a waste collector 42.

Figure 4:
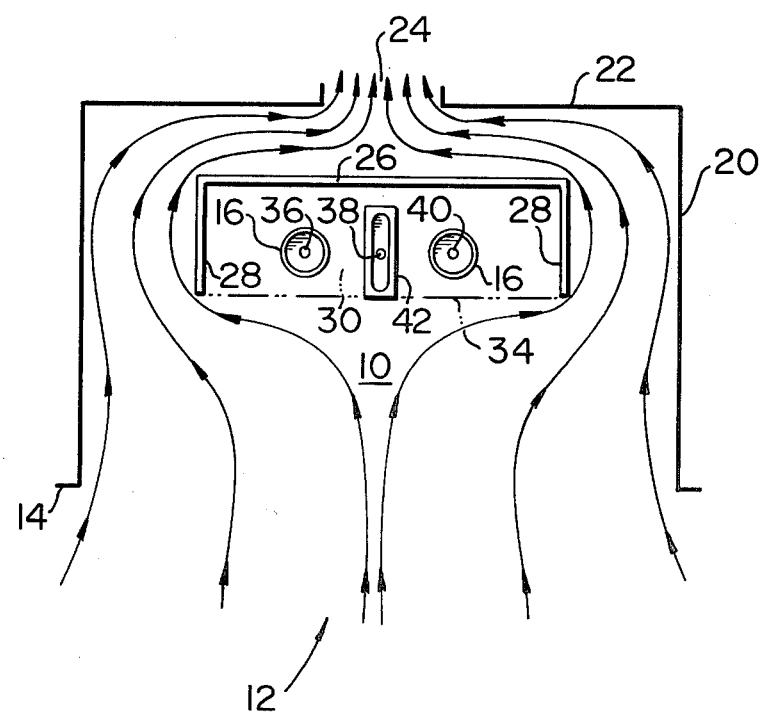

The size, shape and positioning of the diverter member 26 relative to the walls of the chamber 10 and the droplet streams 36, 38 and 40 can, within limits, be dictated by mechanical constraints and convenience of assembly relative to the testing chamber 10 and its other contents, without deteriorating materially the formation of the stagnation region. Generally speaking, the diverter member should be at least tall enough to lie behind the entire length of the droplet streams, and somewhat wider than the distance between the streams as they fan sideward when descending toward the collectors 16, 18 and 42. If the diverter member 26 extends significantly sideward of the droplet streams as in FIG. 3, then most of the containment air flow likewise will move in such direction and no appreciable amount will enter into the stagnation region 30. It thus will be appreciated that the term "stagnation region" is not to be considered as requiring a total absence of containment air flow. The closer the diverter of FIGS. 1-3 lies to the droplet streams, the further forward will extend the stagnation region 30. The forwardly extending sides 28 of the member 26, as shown in FIG. 4, permit the member to be effective with less width and in fact define a more rectangularly shaped stagnation region. One possible disadvantage of the embodiment of FIG. 4 is that the sides 28 might inhibit easy manual access to the sample collectors 16 and 18.

The diverter member 26 should be spaced from the rear wall 22 sufficiently so that the air flow to and through the exhaust port 24 is not inhibited nor forced to bounce along the walls of the sorting chamber to an extent which would cause turbulence and thereby invade and deteriorate the stagnation region. The exhaust port 24 and the diverter member 30 generally should be centered with respect to the sample streams, so that substantially equal amounts of biohazard containment air flow moves in front of and then around the sample streams and obtains a balanced condition for retaining the general shape of the stagnation region. There may exist an engineering design situation which prohibits the port 24 to be in the rear wall 22 and also centered with respect to the surface of the diverter. If so, a plenum 46 can be positioned as shown in FIG. 2 so that its input port 24' acts as the exhaust port, and its open rear side lies along the rear wall 22, which then can have an off center exit port 48. The plenum 46 also could be mounted on the outside surface of the rear wall 22, an arrangement not illustrated. In such case, the exhaust port 24 would be in the rear wall 22 and centered relative to the diverter as in FIG. 1, but then the plenum port 24' would be an exit port and be off centered to the extent necessary.

Structure for generating the originating stream of biological sample material, detecting the particles therein, sensing their characteristics, developing the droplets of sample and deflecting same for sorting purposes, all are old and well known to those skilled in the art. Reference is made to the hereinabove cited patents which, to the extent that a full appreciation of the present invention may require, are hereby incorporated by reference. A portion of such structure is shown in FIGS. 1 and 2 and includes a nozzle 50 and an acoustic coupler 52 which is to be driven by a vibrator 54 so that sample fluid leaving the nozzle is separated into a stream of droplets 56. At least one particle or cell parameter sensor is located within the nozzle and generates a signal so that selected particle containing droplets in the stream 56 can be charged selectively by electrical potential by means including an element 58. The thus selectively charged droplets flow past electrical deflection plates 60 and are deflected proportional to their particle charges and form the separate sample droplet streams 36, 38 and 40. If the sample materials or the liquid in which they flow contain biohazardous substances, the generation of the droplets in air, the movement of the streams in air, and the falling of the droplets into and onto the collectors 16, 18 and 42 can form aerosols and fumes carrying the biohazardous substances forward of the sorting chamber 10 and be inhaled or otherwise cause a dangerous condition to those in the environment of the cell sorter, were it not for the subject biohazard containment method and apparatus.

The air flow diverter member 26 could cause undesirable deflection of the streams of charged droplets if the member 26 were permitted to hold static electrical charge. To minimize the buildup of static electric charge, the member 26 is grounded electrically, as depicted by the chassis ground symbol 62, shown in FIG. 2. Plastic materials exhibit greater tendencies to accumulate static charge and also are more difficult to be grounded efficiently. Hence, metal, such as aluminum is a preferred material for the diverter member.

The remainder of the subject apparatus can comprise state of the art air filtering and air moving elements 64 and 66 as depicted in FIG. 2 and coupled to the exhaust conduits 44 and 45. Known HEPA (high efficiency particulate air) filters capable of retaining over 99% of mono disperse aerosols of 0.3 $\mu$m particles are available as replaceable and disposable elements. The air mover 66 can be a blower having its intake side connected to the output side of the filter 64 for establishing the desired negative pressure at the front face of the chamber 10. The selection of an appropriate air mover to meet design criteria, especially including the generation of sufficient air flow rate at the front face opening 12 to meet biohazard containment specifications, would be a routine engineering matter and would not be made difficult because of the fear of generating air flow that would deflect the sample streams. Experimentation has shown that containment air flow velocities well in excess of the HEW suggested one hundred feet per minute has not caused detrimental sample stream deflection, when the subject diverter member and the resulting stagnation region have been provided. Without the present invention, face air velocities which approximate this magnitude have generated significant sample droplet stream deflection. In lieu of, or in addition to the filter 64 there can be employed known forms of air scrubbers and also the exhaust air can be subjected to incineration.

Although only two configurations of the diverter member 26 have been illustrated and discussed, it now should be apparent that other forms could be employed successfully. For example, as a compromise between the embodiments in FIGS. 3 and 4, the diverter could be arcuate, with its ends forward facing like the sides 28 in FIG. 4. Yet also, the planar shape in FIG. 3 could be bent at a position behind the collector 42, so as to form two divergent portions that are directed forwardly, but still lie behind the sample streams.

It is believed that this invention has been disclosed sufficiently for those skilled in the art to appreciate same and enable them to practice the invention, not only specifically as embodied herein, but in various forms as encompassed by the full scope of the invention as set forth in the claims appended hereto.

What is sought to be protected by United States Letters Patent is:

We claim:

1. Method for use in containment of hazardous substances which may be carried in a stream of biological sample flowing in air within a testing chamber, the testing chamber having at least one face out through which the hazardous substances could move; said method comprising the steps of: establishing a flow of containment air into the chamber through its face and out from the chamber via an exhaust port, the linear face velocity of the containment air flow being sufficient to inhibit hazardous substance movement through the face of the chamber, but of such velocity magnitude to cause detrimental deflection of the biological sample stream if the containment air were to impinge upon the sample stream; and generating an air stagnation region which encompasses the sample stream for preventing the containment air flow from causing detrimental deflection of the sample stream, said generating being accomplished by interposing air flow diverting means between the sample stream and the exhaust port and including diverting the containment air flow generally uniformally laterally with respect to the sample stream, by centering the exhaust port relative to the diverting means, said generating being accomplished in the absence of any air flow shielding structure lying between the chamber face and the sample stream.

2. Method according to claim 1 including grounding electrically the diverting means to inhibit the buildup thereon of static electrical charge.

3. Apparatus for use in containment of hazardous substances which may be carried in a stream of biological sample flowing in air within a testing chamber, the testing chamber having at least one face out through which the hazardous substances could move, the chamber having an exhaust port; said apparatus comprising: means for establishing a flow of containment air into the chamber through its face and out from the chamber via the exhaust port; and means for generating an air stagnation region which encompasses the sample stream in the absence of any air flow shielding structure lying between the chamber face and the sample stream; said means for generating said air stagnation region includes an air flow diverter means interposed between the sample stream and the exhaust port; said diverter means is a generally planar member which is positioned behind the sample stream and has a height which approximates the height of the sample stream and has a width which is significantly wider than the sample stream; and said exhaust port passes through a wall of said testing chamber and said diverter means is spaced from said wall and lies generally parallel thereto.

4. Apparatus according to claim 3 in which the sample stream comprises a plurality of streams of droplets, these streams being laterally separate from each other, and said diverter member extends laterally beyond the sample streams.

5. Apparatus according to claim 3 in which said diverter means includes forward projecting sides for aiding in defining the depth of the air stagnation region.

6. Apparatus according to claim 3 in which said diverter means is grounded electrically to inhibit the buildup thereon of static electrical charge.

* * * * *